(12) United States Patent
Haberger et al.

(10) Patent No.: US 8,524,470 B2
(45) Date of Patent: Sep. 3, 2013

(54) ENZYMATIC ANTIBODY PROCESSING

(75) Inventors: Markus Haberger, Munich (DE); Christine Jung, Iffeldorf (DE); Dietmar Reusch, Munich (DE)

(73) Assignee: Hoffman-La Roche, Inc., Nutley, NJ (US)

( * ) Notice: Subject to any disclaimer, the term of this patent is extended or adjusted under 35 U.S.C. 154(b) by 20 days.

(21) Appl. No.: 13/388,002

(22) PCT Filed: Jul. 28, 2010

(86) PCT No.: PCT/EP2010/004622
§ 371 (c)(1),
(2), (4) Date: Jan. 30, 2012

(87) PCT Pub. No.: WO2011/012297
PCT Pub. Date: Feb. 3, 2011

(65) Prior Publication Data
US 2012/0129216 A1    May 24, 2012

(30) Foreign Application Priority Data
Jul. 30, 2009  (EP) .................................. 09166845

(51) Int. Cl.
*C12P 21/06* (2006.01)
*A23J 1/00* (2006.01)

(52) U.S. Cl.
USPC ........................... 435/68.1; 530/412; 530/413

(58) Field of Classification Search
None
See application file for complete search history.

(56) References Cited

U.S. PATENT DOCUMENTS

| | | | |
|---|---|---|---|
| 5,202,238 | A | 4/1993 | Fell et al. |
| 5,204,244 | A | 4/1993 | Fell et al. |
| 2007/0036883 | A1* | 2/2007 | Schaffer et al. .................. 426/34 |

FOREIGN PATENT DOCUMENTS

| | | |
|---|---|---|
| EP | 0255153 B1 | 1/1995 |
| EP | 0698793 B1 | 12/2004 |
| EP | 1878747 A1 | 1/2008 |
| WF | 2008/057634 A2 | 5/2008 |
| WO | 97/16064 A1 | 5/1997 |
| WO | 97/41232 A1 | 11/1997 |
| WO | 98/33523 A1 | 8/1998 |
| WO | 98/52976 A1 | 11/1998 |
| WO | 00/34317 A2 | 6/2000 |
| WO | 00/34317 A3 | 6/2000 |
| WO | 2005/100394 A2 | 10/2005 |
| WO | 2005/100394 A3 | 10/2005 |
| WO | 2005/100395 A2 | 10/2005 |
| WO | 2005/100395 A3 | 10/2005 |
| WO | 2007/024743 A2 | 3/2007 |
| WO | 2007/024743 A3 | 3/2007 |
| WO | 2007/071347 A2 | 6/2007 |
| WO | 2007/071347 A3 | 6/2007 |
| WO | 2008/057634 A3 | 5/2008 |

OTHER PUBLICATIONS

Jostock T and Li J. (2010). Expression of IgG Antibodies in Mammalian cells. Antibody Engineering, vol. I, $2^{nd}$ Ed., p. 517-529.*
Qian et al. "Structural characterization of N-linked oligosaccharides on monoclonal antibody cetuximab by the combination of orthogonal matrix-assisted laser desorption/ionization hybrid quadrupole-quadrupole time-of-flight tandem mass spectrometry and sequential enzymatic digestion" Analytical Biochemistry 364 (2007) 8-18.*
Feurtado et al. The cloning and characterization of alpha-galactosidase present during and following germination of tomato (*Lycopersicon esculentum* Mill.) seed, J. Experimental Botany, 52(359), 2001, pp. 1239-1249.*
Ashford et al., "Site-specific glycosylation of recombinant rat and human soluble CD4 variants expressed in chinese hamster ovary cells" J. Biol. Chem. 268:3260-3267 ( 1993).
Basu and Basu, "Enzymatic synthesis of a blood group B-related pentaglycosylceramide by an α-galactosyltgransferase from rabbit bone marrow" J. Biol. Chem. 248:1770-1706 ( 1973).
Betteridge and Watkins, "Two α-3-D-galactosyltransferases in rabbit stomach mucosa with different acceptor substrate specificities" Eur. J. Biochem. 132:29-35 ( 1983).
Blake and Goldstein, "An α-D-galactosyltransferase activity in Ehrlich ascites tumor cells" J Biol. Chem. 256:5387-5393 ( 1981).
Blanken and Van den Eijnden, "Biosynthesis of terminal Galα1→3Galβ1→4GlcNAc-Roligosaccharide sequences on glycoconjugates" J. Biol. Chem. 260:12927-12934 ( 1985).
Brueggemann et al., "Comparison of the effector functions of human immunoglobulins using a matched set of chimeric antibodies" J. Exp. Med. 166:1351-1361 ( 1987).
Cummings and Mattox, "Retinoic acid-induced differentiation of the mouse teratocarcinoma cell line F9 is accompanied by an increase in the activity of UDP-galactose:β-D-Galactosyl-α1,3-galactosyltransferase" J. Biol. Chem. 263:511-519 ( 1988).
Dabkowski et al., Transplant Proc. 25:2921 (Oct. 1993).
Elices et al., "Purification and characterization of a UDP-Gal:β:-D-Gal(1,4)-D-GlcNAcα(1,3)-galactosyltransferase from Ehrlich ascites tumor cells" J. Biol. Chem. 261:6064-6072 (May 5, 1986).
Galili et al., "Human natural anti-α-galactosyl IgG; II. The specific recognition of α(1→3)-linked galactose residues" J. Exp. Med. 162:573-582 ( 1985).
Galili et al., "Man, apes, and old world monkeys differ from other mammals in the expression α-galactosyl epitopes on nucleated cells" J. Biol. Chem. 263:17755-17762 ( 1988).

(Continued)

*Primary Examiner* — Daniel E Kolker
*Assistant Examiner* — James Rogers
(74) *Attorney, Agent, or Firm* — Janet M. Martineau

(57) ABSTRACT

The current invention comprises a method for producing an immunoglobulin or immunoglobulin fragment with defined glycostructure comprising the following steps: a) providing an affinity chromatography column eluate containing the immunoglobulin or immunoglobulin fragment, b) incubating the affinity chromatography column eluate with (α1,3)galactosidase of plant origin, e.g. from green coffee beans (EC 3.2.1.22), c) applying the incubated affinity chromatography column eluate to a protein A chromatography material and recovering the immunoglobulin or immunoglobulin fragment from the protein A chromatography material and thereby producing an immunoglobulin or immunoglobulin fragment with defined glycostructure.

10 Claims, 3 Drawing Sheets

(56) References Cited

OTHER PUBLICATIONS

Galili et al., "The human natural anti-Gal IgG; III. The subtley of immune tolerance in man as demonstrated by crossreactivity between natural anti-Gal and Anti-B antibodies" J. Exp. Med. 165:693-704 (1987).

Geisse et al., "Eukaryotic Expression Systems: A Comparison" Protein Expres Purif 8:271-282 (1996).

Jefferis, Royston, "Glycosylation of recombinant antibody therapeutics" Biotechnol Prog 21(1):11-16 (Jan. 2005).

Kaufman, "Overview of Vector Design for Mammalian Gene Expression" Mol Biotechnol 16:151-160 (2000).

Lonberg, N., "Human antibodies from transgenic animals" Nat Biotechnol 23(9):1117-11125 (2005).

Love et al., "Recombinant antibodies possessing novel efector functions" Methods Enzymol. 158:515-527 (1989).

Makrides, S.C., "Components of Vectors for Gene Transfer and Expression in Mammalian Cells" Protein Express Purif 17:183-202 (1999).

Mizuochi et al., "Structures of the sugar chains of mouse immunoglobulin G [1]" Arch Biochem Biophys 257(2):387-394 (1987).

Morrison et al., "Chimeric human antibody molecules: Mouse antigen-binding domains with human constant region domains" P Natl Acad Sci USA 81(21):6851-6855 (Nov. 1984).

Neuberger et al., "A hapten-specific chimaeric IgE antibody with human physiological effector function" Nature 314:268-270 (Mar. 21, 1985).

Parekh et al., "Association of rheumatoid arthritis and primary osteoarthritis with changes in the glycosylation pattern of total serum IgG" Nature 316:452-457 (1985).

Presta, L. G., "Engineering of therapeutic antibodies to minimize immunogenicity and optimize function" Adv Drug Deliver Rev 58:640-656 (2006).

Raju, T. S., "Glycosylation variations with expression systems and their impact on biological activity of therapeutic immunoglobulins" BioProcess International 1:44-53 (2003).

Riechmann et al., "Reshaping human antibodies for therapy" Nature 332:323-327 (Mar. 24, 1988).

Routier et al., "The glycosylation pattern of a humanized IgGI antibody (D1.3) expressed in :CHO cells" Glycoconjugate J 14:201-207 (1997).

Saba et al., "A study of immunoglobulin G glycosylation in monoclonal and polyclonal species by electrospray and matrix-assisted laser desorption/ionization mass spectrometry" Anal Biochem 305(1):16-31 (Jun. 1, 2002).

Shaper et al., "β1,4-Galactosyltransferase and lactose biosynthesis: recruitment of a housekeeping gene from the nonmammalian vertebrate gene pool for a mammary gland specific function" J. Mamm. Gland Biol. Neopl. 3:315-324 (1998).

Taniguchi et al., "Structures of the sugar chains of rabbit immunoglobulin G: Occurrence of asparagine-linked sugar chains in Fab fragment" Biochemistry—US 24:5551-5557 (1985).

Vijayalakshmi, "Antibody purification methods" Appl Biochem Biotech 75:93-102 (1998).

Werner et al., "Appropriate mammalian expression systems for biopharmaceuticals" Arznei-Forschung/Drug Res 48(8):870-880 (1998).

Yamamoto et al., "Molecular genetic basis of the histo-blood group ABO system" Nature 345:229-233 (1990).

\* cited by examiner

ENZYMATIC ANTIBODY PROCESSING

This application is a national stage entry of International Application No. PCT/EP2010/004622, filed Jul. 28, 2010, which claims the benefit of European Patent Application No. EP 09166845.9, filed Jul. 30, 2009. The contents of these Applications are hereby incorporated by reference in their entirety.

The current invention is directed to a method for enzymatic downstream processing of recombinantly produced immunoglobulins. In more detail the current invention is directed to a method for modification of the (α1,3)glycosidically bound galactose content of full length immunoglobulins or immunoglobulin Fc-parts after an affinity chromatography by an enzymatic treatment.

BACKGROUND OF THE INVENTION

Polypeptides obtained from eukaryotic cells are produced as glycosylated polypeptides. The glycostructures are attached to the amino acid backbone as post-translational enzymatic modification.

The glycosyltransferases are recognized as a functional family of estimated 250-300 different intracellular, membrane-bound enzymes that participate in the coordinate biosynthesis of the glycostructures of polypeptides, including glycoproteins, proteoglycans and glycolipids. The glycosyltransferases are classified into groups based on their nucleotide monosaccharide donor specificity. For example, the galactosyltransferases are the subset of glycosyltransferases that use UDP-galactose as the activated monosaccharide donor whereas the sialyltransferases use CMP-sialic acid and the fucosyltransferases use GDP-fucose (Shaper, N. L., et al., J. Mamm. Gland Biol. Neopl. 3 (1998) 315-324).

The modification of alpha-galactosyl epitopes on various mammalian cells is of particular interest, since as much as 1% of circulating IgG antibodies in humans interact with this oligosaccharide residue. This natural antibody, designated "anti-Gal", was previously found to bind to terminal Gal(α1,3)Gal(β1,4)GlcNAc-R on biochemically defined glycolipids (Galili, U., et al., J. Exp. Med. 162 (1985) 573-582; Galili, U., et al., J. Exp. Med. 165 (1987) 693-704). Measurement of the binding of radiolabeled Bandeiraea (Griffonia) simplicifolia IB4 lectin to the various nucleated cells suggests that cells binding anti-Gal express $10^6$ to $3.5 \times 10^7$ alpha-galactosyl epitopes, most of which, based on the anti-Gal specificity, seem to have the structure of Gal(α1,3)Gal(β1,4)GlcNAc-R. The absence of these epitopes from human cells results from diminished activity of the enzyme (α1,3)galactosyltransferase (Galili, U., et al., J. Biol. Chem. 263 (1988) 17755-17762).

The synthesis of the Gal(α1,3)epitope in the Golgi apparatus of cells of murine origin (Cummings, R. D. and Mattox, S. A., J. Biol. Chem. 263 (1988) 511-519; Blake, D. A., and Goldstein, I. J., J. Biol. Chem. 256 (1981) 5387-5393; Elices, M. J., Blake, D. A., and Goldstein, I. J. J. Biol. Chem. 261 (1986) 6064-6072), leporine origin (Basu, M., and Basu, S., J. Biol. Chem. 248 (1973) 1700-1706; Betteridge, A., and Watkins, W. M., Eur. J. Biochem. 132 (1983) 29-35), porcine origin and bovine origin (Blanken, W. M., and Van den Eijnden, D. H., J. Biol. Chem. 260 (1985) 12927-12934) has been demonstrated to be catalyzed by the enzyme (α1,3) galactosyltransferase.

In polypeptides which are intended for application to humans the presence of (α1,3)glycosidically bound terminal galactose residues should be minimized as this glycostructure will elicit a response by the human immune system. This can be achieved, for example, by the time-consuming development of cell lines for the recombinant production of the therapeutic polypeptide which do not introduce (α1,3)glycosidically bound terminal galactose residues in the glycostructures of the therapeutic polypeptide. With chromatographic method generally used in the downstream processing of the crude polypeptide the Gal(α1,3)-containing glycostructures cannot be removed.

In EP 0 255 153 a process for producing α-galactosidase capable of decreasing the galactose content of galactomannans by splitting off 1,6 linked alpha-D-galactopyranosyl units attached to a main chain of 1,4 linked beta-D-mannopyranosyl units is reported. A method for clinical examination based on the structures of immunoglobulin G-linked oligosaccharides is reported in EP 0 698 793. In EP 1 878 747 glyco-engineered antibodies are reported. Selective marking of immunoglobulin glycans is reported in WO 2007/071347. In WO 1997/016064 methods and compositions for the reduction of xenotransplantation rejection are reported. Antibody preparations with substantially homogeneous and unsialylated glycoforms, such as G0 and G2, which are prepared by enzymatic treatment, expression under certain conditions, use of particular host cells, and contact with serum, are reported in WO 2007/024743.

In WO 2008/057634 polypeptides with enhanced anti-inflammatory and decreased cytotoxic properties and relating methods are reported. Proteolysis resistant antibody preparations are reported in WO 2007/024743.

SUMMARY OF THE INVENTION

It has been found that an (α1,3)galactosidases from plant origin, e.g. from green coffee beans (EC 3.2.1.22), can be used to selectively remove (α1,3)glycosidically bound terminal galactose residues from the oligosaccharide at amino acid Asn297 in an immunoglobulin CH2 domain. (α1,3)galactosidases from non-plant origin were found to have (β1,4)galactosidases side reactivity and/or were less or not-reactive with tri- or tetra-antennary oligosaccharides.

Thus, herein is reported a method for producing an immunoglobulin or immunoglobulin fragment with defined glycostructure comprising the following steps in the following order:
  providing an affinity chromatography column eluate containing the immunoglobulin or immunoglobulin fragment,
  incubating the affinity chromatography column eluate with an enzyme, which cleaves off the terminal monosaccharide residues of the glycostructure in the CH2 domain of the immunoglobulin or immunoglobulin fragment,
  applying the incubated affinity chromatography eluate to a protein A chromatography material under conditions suitable for binding of the immunoglobulin or immunoglobulin fragment to the protein A chromatography material and recovering the immunoglobulin or immunoglobulin fragment from the protein A chromatography material and thereby producing an immunoglobulin or immunoglobulin fragment with defined glycostructure.

In one embodiment the enzyme, which cleaves off the monosaccharide residue at the non-reducing end of the glycostructure in the CH2 domain of the immunoglobulin or immunoglobulin fragment, is of plant origin. In one embodiment the enzyme, which cleaves off the monosaccharide residue at the non-reducing end of the glycostructure in the CH2 domain of the immunoglobulin or immunoglobulin fragment, is selected from α-D-galactoside galactohydrolase (EC 3.2.1.22) or Melibiase. In another embodiment the enzymes is (α1,3)galactosidase from green coffee beans (EC 3.2.1.22). In another embodiment the terminal monosaccharide residue of the glycostructure in the CH2 domain of the immunoglobulin or immunoglobulin fragment is an (α1,3)glycosidically bound galactose residue.

In one embodiment the incubating the affinity chromatography column eluate with an enzyme, which cleaves off the monosaccharide residue at the non-reducing end of the glycostructure in the CH2 domain of the immunoglobulin or immunoglobulin fragment, comprises the following steps:
  incubating the affinity chromatography column eluate with an (α1,3)glycosidase,
  taking a sample from the incubation mixture,
  either
    applying the sample to protein A coated sepharose beads and afterwards washing the beads,
    recovering the immunoglobulin or immunoglobulin fragment from the protein A sepharose beads,
    adjusting the buffer conditions for glycosidase/sialidase digest,
    incubating the immunoglobulin or immunoglobulin fragments with a glycosidase/sialidase to cleave of all N-Glycans, and
    taking an aliquot of the digest prior to MALDI analysis,
  or
    applying the sample to protein A coated magnetic beads and afterwards washing the beads,
    incubating the beads with a glycosidase and recovering the cleaved off oligosaccharides, and
    purifying the cleaved off oligosaccharides with a cation exchange chromatography,
  determining the kind and amount of the monosaccharide residue at the non-reducing end of the glycostructure in the cleaved off oligosaccharides by mass spectrometry,
  continuing the incubating until all monosaccharide residue at the non-reducing end of the glycostructures, which can be cleaved off by the enzyme, have been cleaved off.

In still a further embodiment comprises the method the following steps in the following order as first steps:
  providing a cell comprising a nucleic acid encoding the immunoglobulin or immunoglobulin fragment,
  cultivating the cell under conditions suitable for the expression of the immunoglobulin or immunoglobulin fragment,
  recovering the immunoglobulin or immunoglobulin fragment from the cell or the cultivation medium,
  applying the immunoglobulin or immunoglobulin fragment to a protein A chromatography material under conditions suitable for binding of the immunoglobulin to the protein A chromatography material and recovering the immunoglobulin from the protein A chromatography material.

In one embodiment comprises the method the following step as final step:
  purifying the produced immunoglobulin or immunoglobulin fragment with a defined glycostructure with one to three chromatography steps.

In one embodiment the enzyme, which cleaves off the monosaccharide residue at the non-reducing end of the glycostructure in the CH2 domain of the immunoglobulin or immunoglobulin fragment, is of plant origin. In another embodiment the enzyme, which cleaves off the monosaccharide residue at the non-reducing end of the glycostructure in the CH2 domain of the immunoglobulin or immunoglobulin fragment, is selected from α-galactosidase, β-galactosidase, mannosidase, fucosidase, or sialidase. In a further embodiment the cell is a mammalian cell. In another embodiment the mammalian cell is a hamster cell, or murine cell, or a rabbit cell, or a sheep cell, or a hybridoma cell thereof. In still a further embodiment the cell is a CHO cell, a NS0 cell, a BHK cell or a SP2/0 cell.

A further aspect as reported herein is the use of an (α1,3) galactosidase from green coffee beans (EC 3.2.1.22) for cleaving off the terminal (α1,3)glycosidically bound galactose residues from the glycostructures in the CH2 domain of a recombinantly produced immunoglobulin or immunoglobulin fragment.

DETAILED DESCRIPTION OF THE INVENTION

Herein is reported that e.g. (α1,3)galactosidases from green coffee beans (EC 3.2.1.22) can be used to selectively remove (α1,3)glycosidically bound terminal galactose residues from the oligosaccharide attached at amino acid residue Asn297 to an immunoglobulin CH2 domain. (α1,3)galactosidases from other sources beside plants were found to have (β1,4)galactosidases side reactivity and/or were less or not-reactive with tri- or tetra-antennary oligosaccharides (see Table 1).

TABLE 1

Comparison of (α1,3)galactosidases from different sources

| (α1,3)galacto-sidase from (EC 3.2.1.22) | cleave off of (α1,3)glycosi-dically bound galactose | cleave off of (α1,4)glycosi-dically bound galactose | cleave off of oligosaccharides | |
|---|---|---|---|---|
| | | | bi-antennary | tri- and tetra-antennary |
| green coffee bean | yes | no | yes | yes |
| Xanthomonas manihotis | yes | yes | yes | yes |
| Escherichia coli | yes | yes | yes | no |

Thus, in one embodiment the enzyme in the methods as reported herein, which cleaves off the terminal monosaccharide residues of the glycostructure in the CH2 domain of the immunoglobulin or immunoglobulin fragment, is of plant origin. In another embodiment the enzyme in the methods as reported herein, which cleaves off the terminal monosaccharide residues of the glycostructure in the CH2 domain of the immunoglobulin or immunoglobulin fragment, is an enzyme that (i) cleaves off (α1,3)glycosidically bound sugar residues, and (ii) does not cleave off (α1,4)glycosidically bound sugar residues, and (iii) cleaves off the residues from bi-, tri-, and tetra-antennary oligosaccharides.

Herein is reported a method for producing an immunoglobulin or immunoglobulin fragment with defined glycostructure comprising the following steps:
  providing an affinity chromatography column eluate containing the immunoglobulin or immunoglobulin fragment,
  incubating the affinity chromatography column eluate with the (α1,3)-galactosidase from green coffee beans (EC 3.2.1.22),
  applying the incubated affinity chromatography column eluate to a protein A chromatography material, optionally under conditions suitable for binding of the immunoglobulin or immunoglobulin fragment to the protein A chromatography material, and recovering the immunoglobulin or immunoglobulin fragment from the protein A chromatography material and thereby producing an immunoglobulin or immunoglobulin fragment with defined glycostructure.

Human immunoglobulins are mainly glycosylated at the asparagine residue at position 297 (Asn297) of the heavy chain CH2 domain with a core fucosylated biantennary complex oligosaccharide (immunoglobulin amino acid residue numbering according to Kabat, see below). The biantennary glycostructure can be terminated by up to two consecutive galactose (Gal) residues in each arm. The arms are denoted (1,6) and (1,3) according to the glycoside bond to the central mannose residue. The glycostructure denoted as G0 comprises no galactose residue. The glycostructure denoted as G1 contains one or more galactose residues in one arm. The glycostructure denoted as G2 contains one or more galactose residues in each arm (Raju, T. S., Bioprocess Int. 1 (2003) 44-53). Human constant heavy chain regions are reported in detail by Kabat, E. A., et al., Sequences of Proteins of Immunological Interest, 5th Ed. Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527. CHO type glycosylation of immunoglobulin Fc parts is e.g. described by Routier, F. H., Glycoconjugate J. 14 (1997) 201-207.

The term "immunoglobulin" denotes and encompasses the various forms of immunoglobulins such as human immunoglobulins, humanized immunoglobulins, chimeric immunoglobulins, or T-cell antigen depleted immunoglobulins (see e.g. WO 98/33523, WO 98/52976, and WO 00/34317). In one embodiment the antibody in the methods as reported herein is a human or humanized antibody. Genetic engineering of immunoglobulins is e.g. described in Morrison, S. L., et al., Proc. Natl. Acad Sci. USA 81 (1984) 6851-6855; U.S. Pat. No. 5,202,238 and U.S. Pat. No. 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125.

An immunoglobulin in general comprises two so called full length light chain polypeptides (light chain) and two so called full length heavy chain polypeptides (heavy chain). Each of the full length heavy and light chain polypeptides contains a variable domain (variable region) (generally the amino terminal portion of the full length polypeptide chain) comprising binding regions which interact with an antigen. Each of the full length heavy and light chain polypeptides comprises a constant region (generally the carboxyl terminal portion). The constant region of the full length heavy chain mediates the binding of the immunoglobulin i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of a full length immunoglobulin's light or heavy chain in turn comprises different segments, i.e. four framework regions (FR) and three hypervariable regions (CDR). A "full length immunoglobulin heavy chain" is a polypeptide consisting in N-terminal to C-terminal direction of an immunoglobulin heavy chain variable domain (VH), an immunoglobulin constant domain 1 (CH1), an immunoglobulin hinge region, an immunoglobulin constant domain 2 (CH2), an immunoglobulin constant domain 3 (CH3), and optionally an immunoglobulin constant domain 4 (CH4) in case of an immunoglobulin of the subclass IgE. A "full length immunoglobulin light chain" is a polypeptide consisting in N-terminal to C-terminal direction of an immunoglobulin light chain variable domain (VL), and an immunoglobulin light chain constant domain (CL). The full length immunoglobulin chains a linked together via inter-polypeptide disulfide bonds between the CL-domain and the CH1 domain and between the hinge regions of the full length immunoglobulin heavy chains.

The term "immunoglobulin fragment" denotes within this application a polypeptide comprising at least the CH2 domain and the CH3 domain of a full length immunoglobulin heavy chain. An immunoglobulin fragment may also comprise additional non-immunoglobulin derived amino acid sequences.

Is has been reported in recent years that the glycosylation pattern of immunoglobulins, i.e. the saccharide composition and multitude of attached glycostructures, has a strong influence on the biological properties (see e.g. Jefferis, R., Biotechnol. Prog. 21 (2005) 11-16). Immunoglobulins produced by mammalian cells contain 2-3% by mass oligosaccharides (Taniguchi, T., et al., Biochem. 24 (1985) 5551-5557). This is equivalent e.g. in an immunoglobulin of class G (IgG) to 2.3 oligosaccharide residues in an IgG of mouse origin (Mizuochi, T., et al., Arch. Biochem. Biophys. 257 (1987) 387-394) and to 2.8 oligosaccharide residues in an IgG of human origin (Parekh, R. B., et al., Nature 316 (1985) 452-457), whereof generally two are located in the Fc-region at $Asn^{297}$ and the remaining in the variable region (Saba, J. A., et al., Anal. Biochem. 305 (2002) 16-31).

The term "glycostructure" as used within this application denotes and comprises all oligosaccharides which are attached to a specified amino acid residue in an immunoglobulin. Due to the glycosylation heterogeneity of a cell, a recombinantly produced immunoglobulin comprises not only a single, defined N- or O-linked oligosaccharide at a specified amino acid residue, but is a mixture of polypeptides (immunoglobulin molecules) each having the same amino acid sequence but comprising differently composed oligosaccharides at the specified amino acid position. Thus, the term "glycostructure" denotes a group of oligosaccharides that are attached at a specified amino acid position of a recombinantly produced immunoglobulin, i.e. the heterogeneity of the attached oligosaccharide. The term "oligosaccharide" as used within this application denotes a polymeric saccharide comprising two or more covalently linked monosaccharide units.

For the notation of the different N- or O-linked oligosaccharides in the current invention the individual sugar residues are listed from the non-reducing end to the reducing end of the oligosaccharide molecule. The longest sugar chain was chosen as basic chain for the notation. The reducing end of an N- or O-linked oligosaccharide is the monosaccharide residue, which is directly bound to the amino acid of the amino acid backbone of the immunoglobulin, whereas the end of an N- or O-linked oligosaccharide, which is located at the opposite terminus as the reducing end of the basic chain, is termed non-reducing end.

The term "affinity chromatography" as used within this application denotes a chromatography method which employs an "affinity chromatography material". In an affinity chromatography polypeptides are separated based on their biological activity or chemical structure depending on the formation of electrostatic interactions, hydrophobic bonds, and/or hydrogen bonds to the chromatographical functional groups of the chromatography material. To recover the specifically bound polypeptide from the affinity chromatography material either a competitor ligand can be added or the chromatography conditions, such as pH value, polarity or ionic strength of the buffer, can be changed. Exemplary "affinity chromatography materials" are metal chelating chromatography materials such as Ni(II)-NTA or Cu(II)-NTA, or immunoglobulin affinity chromatography materials such as in one embodiment of the methods as reported herein chromatography materials comprising thereto covalently linked protein A or protein G, or enzyme binding affinity chromatography materials such as chromatography materials comprising thereto covalently bound enzyme substrate analogues, enzyme cofactors, or enzyme inhibitors as chromatographical functional group, or lectin binding chromatography materials such as chromatography materials comprising thereto covalently linked polysaccharides, cell surface receptors, glycoproteins, or intact cells as chromatographical functional group.

The term "enzyme, which cleaves off the monosaccharide residue at the non-reducing end of the glycostructure in the CH2 domain of the immunoglobulin or immunoglobulin fragment" denotes an enzyme that selectively cleaves off a monosaccharide residue at the non-reducing end of a glycostructure. Such an enzyme is of plant origin. In one embodiment the enzyme is of plant origin and is selected from $\alpha$-galactosidases (cleaving off of ($\alpha$1,3)-, ($\alpha$1,4)-, and/or ($\alpha$1,6) glycosidically bound galactose residues, $\beta$-galactosidase (cleaving off of ($\beta$1,4)glycosidically bound galactose residues), mannosidase (cleaving off of mannose residues), fucosidase (cleaving off of fucose residues), and sialidase (cleaving off of sialic acid residues). Exemplary $\alpha$-galactosidases are ($\alpha$1,3)galactosidases such as EC 3.2.1.22 or EC 2.4.1.151 (see, e.g., Dabkowski, P. L., et al., Transplant Proc. 25 (1993) 2921 and Yamamoto, F., et al., Nature 345 (1990) 229-233). In one embodiment the enzyme is ($\alpha$1,3)galactosidase from green coffee beans (EC 3.2.1.22).

The term "defined glycostructure" denotes within this application a glycostructure in which the monosaccharide residue at each of the non-reducing ends of the glycostructure is of a specific kind and linked with a specific glycosidic bond to the rest of the glycostructure, i.e. all further monosaccharides residues have been cleaved off. The term "defined glycostructure" denotes within this application a glycostructure in which all monosaccharide residue at the non-reducing end of glycostructures of a specific kind and linked with a specific glycosidic bond to the glycostructure have been cleaved off, i.e. the glycostructures of an immunoglobulin or immunoglobulin fragment are depleted of or lack a specific terminal monosaccharide residue linked via a specific glycosidic bond to the remainder of the glycostructure. For example, if as in one embodiment the immunoglobulin or immunoglobulin fragment is incubated with an ($\alpha$1,3)galactosidase all the glycostructures of the immunoglobulin or immunoglobulin fragment lack ($\alpha$1,3)glycosidically bound galactose monosaccharide residue at the non-reducing end, i.e. the immunoglobulin or immunoglobulin fragment has a defined glycostructure which lacks ($\alpha$1,3)glycosidically bound terminal galactose residues.

The term "applying to" and grammatical equivalents thereof as used within this application denotes a partial step of a purification method in which a solution containing a substance of interest is brought in contact with a stationary phase. The solution containing the substance of interest to be purified passes through the stationary phase providing for an interaction between the stationary phase and the substances in solution. Depending on the conditions, such as e.g. pH, conductivity, salt concentration, temperature, and/or flow rate, some substances of the solution are bound to the stationary phase and therewith are removed from the solution. Other substances remain in solution. The substances remaining in solution can be found in the flow-through. The "flow-through" denotes the solution obtained after the passage of the chromatographic device, which may either be the applied solution containing the substance of interest or the buffer, which is used to flush the column or to cause elution of one or more substances bound to the stationary phase. The substance of interest can be recovered from the solution after the purification step by methods familiar to a person of skill in the art, such as e.g. precipitation, salting out, ultrafiltration, diafiltration, lyophilization, affinity chromatography, or solvent volume reduction to obtain the substance in substantially homogeneous form.

An immunoglobulin or immunoglobulin fragment whose glycostructure can be modified in the methods as reported herein can be produced by recombinant means. Methods for recombinant production are widely known in the state of the art and comprise protein expression in eukaryotic cells with subsequent isolation of the immunoglobulin or immunoglobulin fragment and purification to a pharmaceutically acceptable purity. For the expression of the immunoglobulin or immunoglobulin fragment either a hybridoma cell or a eukaryotic cell, in which one or more nucleic acids encoding the immunoglobulin or immunoglobulin fragment have been introduced, is used. In one embodiment the eukaryotic cells is selected from CHO cells, NS0 cells, SP2/0 cells, HEK 293 cells, COS cells, PER.C6 cells, BHK cells, rabbit cells, or sheep cells. In another embodiment the eukaryotic cell is selected from CHO cells, HEK cells, or rabbit cells. After expression the immunoglobulin or immunoglobulin fragment is recovered from the cells (from the supernatant or from the cells after lysis). General methods for recombinant production of immunoglobulins are well-known in the state of the art and reported, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

Purification of immunoglobulins or immunoglobulin fragments can be performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art (see e.g. Ausubel, F., et al. (ed.), Current Protocols in Molecular Biology, Greene Publishing and Wiley Interscience, New York (1987)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis), as well as combinations thereof, such as affinity chromatography with microbial proteins, cation exchange chromatography and anion exchange chromatography (see e.g. Vijayalakshmi, M. A., Appl. Biochem. Biotech. 75 (1998) 93-102).

The glycostructure of a recombinantly produced immunoglobulin or immunoglobulin fragment will be determined by the employed cell line and the employed cultivation conditions. With conventional down stream processing techniques selective removal of specific glycostructures is not possible.

With the methods as reported herein an immunoglobulin or immunoglobulin fragment with defined glycostructure can be obtained in down stream processing. It has been found that for the removal of ($\alpha$1,3)glycosidically bound galactose residues at the non-reducing end of the glycostructures of immunoglobulins or immunoglobulin fragments an ($\alpha$1,3)galactosidase of plant origin, especially from green coffee beans, is only suited.

The removal of ($\alpha$1,3)glycosidically bound galactose residues during the down stream processing of a recombinantly produced immunoglobulin or immunoglobulin fragment with a method as reported herein provides a method for the reduction of the immunogenicity of a recombinantly produced immunoglobulin or immunoglobulin fragment, abolishes the need to obtain/select/use a cell line that does not produce glycostructures with a terminal ($\alpha$1,3)glycosidically bound galactose residue, does not change the product quality due to the additional incubation step of the immunoglobulin or immunoglobulin fragment compared to a method without the additional incubation, provides a method for producing an immunoglobulin or immunoglobulin fragment with a defined glycostructure during the down stream processing, i.e. after the expression is finished in vitro, provides the immunoglobulin with defined glycostructure with improved yield as no immunoglobulin with unwanted glycostructure is removed but all immunoglobulin is enzymatically converted to a defined glycostructure.

Thus, one aspect as reported herein is a method for producing an immunoglobulin or immunoglobulin fragment with defined glycostructure comprising the following step:

incubating the immunoglobulin or immunoglobulin fragment with an enzyme, which cleaves off specifically a terminal monosaccharide residue of the glycostructure in the CH2 domain of the immunoglobulin or immunoglobulin fragment.

In one embodiment the enzyme, which cleaves off specifically a terminal monosaccharide residues of the glycostructure in the CH2 domain of the immunoglobulin or immunoglobulin fragment, is ($\alpha$1,3)galactosidase from green coffee beans. In another embodiment the terminal monosaccharide is ($\alpha$1,3)glycosidically bound galactose.

Thus, one aspect as reported herein is a method for producing an immunoglobulin or immunoglobulin fragment with defined glycostructure comprising the following steps:

providing an affinity chromatography column eluate containing the immunoglobulin or immunoglobulin fragment, incubating the affinity chromatography column eluate with an enzyme, which cleaves off specifically a terminal monosaccharide residues of the glycostructure in the CH2 domain of the immunoglobulin or immunoglobulin fragment, applying the enzymatically modified affinity chromatography column eluate to a protein A chromatography material and recovering the immunoglobulin or immunoglobulin fragment from the protein A chromatography material and thereby producing an immunoglobulin or immunoglobulin fragment with defined glycostructure.

To monitor the progress of the enzymatic reaction an on-line determination of the glycosylation profile of the immunoglobulin or immunoglobulin fragment can be performed. Therefore, one aspect as reported herein is a method for producing an immunoglobulin or immunoglobulin fragment with defined glycostructure comprising the following steps:

providing an affinity chromatography column eluate containing the immunoglobulin or immunoglobulin fragment, modifying the immunoglobulin or immunoglobulin fragment contained in the affinity chromatography column eluate by
  a) incubating the affinity chromatography column eluate with an enzyme, which cleaves off specifically a terminal monosaccharide residues of the glycostructure in the CH2 domain of the immunoglobulin or immunoglobulin fragment,
  b) taking a sample from the incubation mixture,
  c) applying the sample to protein A coated magnetic beads and afterwards washing the beads,
  d) incubating the beads with a glycosidase and recovering the cleaved-off oligosaccharides,
  e) purifying the cleaved-off oligosaccharides with a cation exchange chromatography,
  f) determining the kind and amount of monosaccharide residue at the non reducing end of the cleaved-off oligosaccharides by mass spectrometry, e.g. by MALDI-TOF MS,
  g) repeating steps a) to f) until all monosaccharide residues at the non-reducing end of the glycostructure of the immunoglobulin or immunoglobulin fragment that can be cleaved off by the enzyme have been cleaved off, applying the enzymatically modified affinity chromatography column eluate to a protein A chromatography material, optionally under conditions suitable for binding of the contained immunoglobulin or immunoglobulin fragment to said protein A chromatography material, and recovering the immunoglobulin or immunoglobulin fragment from the protein A chromatography material and thereby producing an immunoglobulin or immunoglobulin fragment with defined glycostructure.

It has been found that the enzyme ($\alpha$1,3)galactosidase from green coffee beans is surprisingly useful in the methods as reported herein. ($\alpha$1,3)galactosidases from a bacterial source have been evaluated in the methods as reported herein but found to be not suited. Although all these enzymes can cleave an ($\alpha$1,3)glycosidic bond in oligosaccharides only the ($\alpha$1,3)galactosidase from green coffee beans cleaves such a bond in glycostructures of immunoglobulins or immunoglobulin fragments at suitable conditions, with suitable specificity, and with suitable substrate specificity.

A further aspect as reported herein is a method for producing an immunoglobulin or immunoglobulin fragment with defined glycostructure comprising the following steps:

providing a cell comprising a nucleic acid encoding the immunoglobulin or immunoglobulin fragment, cultivating the cell under conditions suitable for the expression of the immunoglobulin or immunoglobulin fragment, recovering the immunoglobulin or immunoglobulin fragment from the cell or the cultivation medium, applying the recovered immunoglobulin or immunoglobulin fragment to a protein A chromatography material and recovering the immunoglobulin from the protein A chromatography material by eluting the immunoglobulin or immunoglobulin fragment from the protein A chromatography material, modifying the immunoglobulin or immunoglobulin fragment contained in the affinity chromatography column eluate by
  a) incubating the affinity chromatography column eluate with an enzyme, which cleaves off specifically a terminal monosaccharide residues of the glycostructure in the CH2 domain of the immunoglobulin or immunoglobulin fragment, b) taking a sample from the incubation mixture, c) applying the sample to protein A coated magnetic beads and afterwards washing the beads, d) incubating the beads with a glycosidase and recovering the cleaved-off oligosaccharides, e) purifying the cleaved-off oligosaccharides with a cation exchange chromatography, f) determining the kind and amount of the monosaccharide residue at the non-reducing end of the cleaved off oligosaccharides by mass spectrometry, e.g. by MALDI-TOF MS, g) repeating steps a) to f) until all monosaccharide residues at the non-reducing end of the glycostructure of the immunoglobulin or immunoglobulin fragment that can be cleaved off by the enzyme have been cleaved off, applying the enzymatically modified affinity chromatography column eluate to a protein A chromatography material and recovering the immunoglobulin or immunoglobulin fragment from the protein A chromatography material and thereby producing an immunoglobulin or immunoglobulin fragment with defined glycostructure.

optionally purifying the produced immunoglobulin or immunoglobulin fragment with a defined glycostructure with one to three additional chromatography steps.

For the purification of immunoglobulins or immunoglobulin fragments, which have been produced e.g. by cell cultivation methods, generally a combination of different chromatography steps can be employed. Normally a protein A affinity chromatography can be followed by one or two additional separation steps. In one embodiment the additional chromatography steps are a cation and an anion exchange chromatography step or vice versa. The final purification step is a so called "polishing step" for the removal of trace impurities and contaminants like aggregated immunoglobulins, residual HCP (host cell protein), DNA (host cell nucleic acid), viruses, or endotoxins. In one embodiment the final purification step is an anion exchange chromatography in flow-through mode.

General chromatographic methods and their use are known to a person skilled in the art. See for example, Chromatography, 5$^{th}$ edition, Part A: Fundamentals and Techniques, Heftmann, E. (ed), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

At the time the invention was made a fusion protein consisting of an N-terminal mutated or non-mutated IL-15 part and a C-terminal Fc part was available in sufficient quantities in our laboratory. This fusion protein has been used as an example and should not be construed to limit the scope of the invention which is defined by the appended claims. Thus, in one embodiment the immunoglobulin or immunoglobulin fragment is a fusion protein of an interleukin-15 part and an Fc part of human origin of SEQ ID NO: 1 or 2. Such a molecule is reported in example 1 and SEQ ID NO: 3 and 4 (with murine Fc part) of WO 2005/100394.

The following examples, figures and sequences are provided to aid the understanding of the present invention, the true scope of which is set forth in the appended claims. It is understood that modifications can be made in the procedures set forth without departing from the spirit of the invention.

Description of the Sequence Listing

SEQ ID NO:1 Nucleic acid sequence of human mutated interleukin 15/Fc.

SEQ ID NO:2 Amino acid sequence of human mutated interleukin 15/Fc.

Example 1

Preparation of Purified Interleukin-15/Fc Fusion Protein

Figure 1:
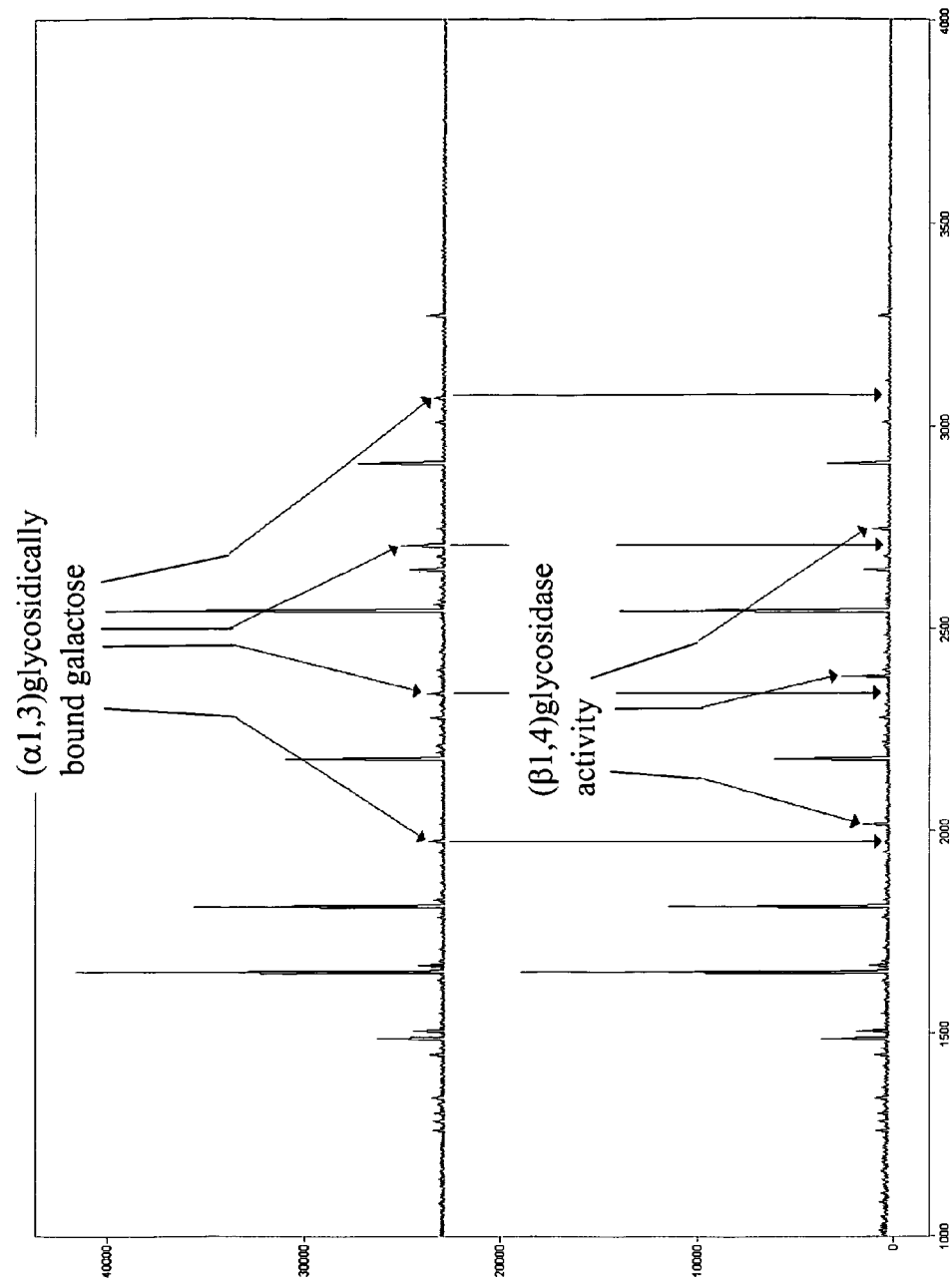
FIG. 1 Total ion chromatogram of the reference sample of a mutated IL15FC-Fc fusion polypeptide (upper part) and of the incubation with the ($\alpha$1,3)galactosidase from *Xanthomonas manihotis* (lower part). It can be seen that this enzyme has also ($\alpha$1,4)galactosidase activity.
Figure 2:
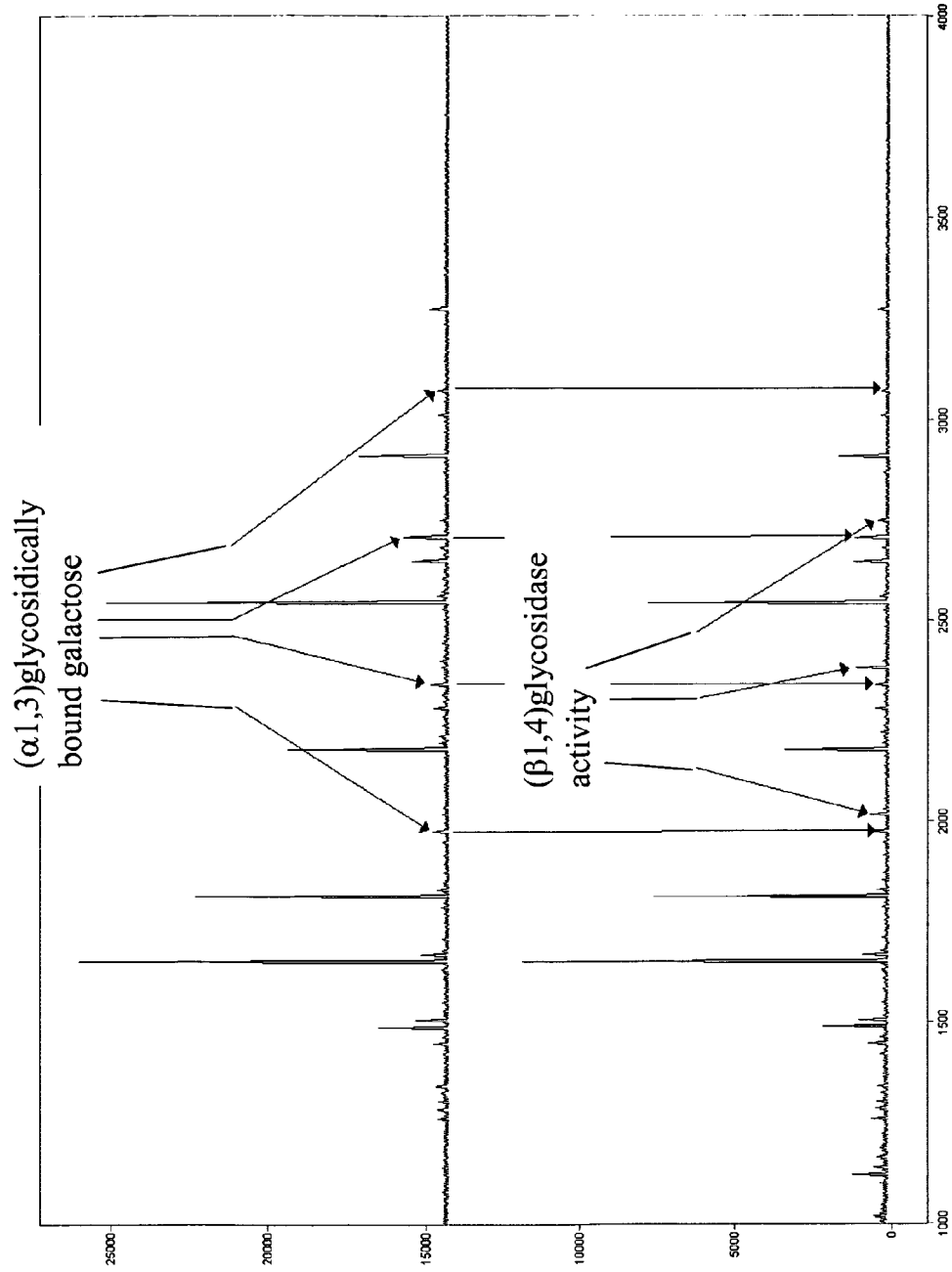
FIG. 2 Total ion chromatogram of the reference sample of a mutated IL15FC-Fc fusion polypeptide (upper part) and of the incubation with the ($\alpha$1,3)galactosidase from *Escherichia Coli* (lower part). It can be seen that ($\alpha$1,3)glycosidically bound galactose was only removed at biantennary oligosaccharides and that this enzyme has also ($\beta$1,4)galactosidase activity.
Figure 3:
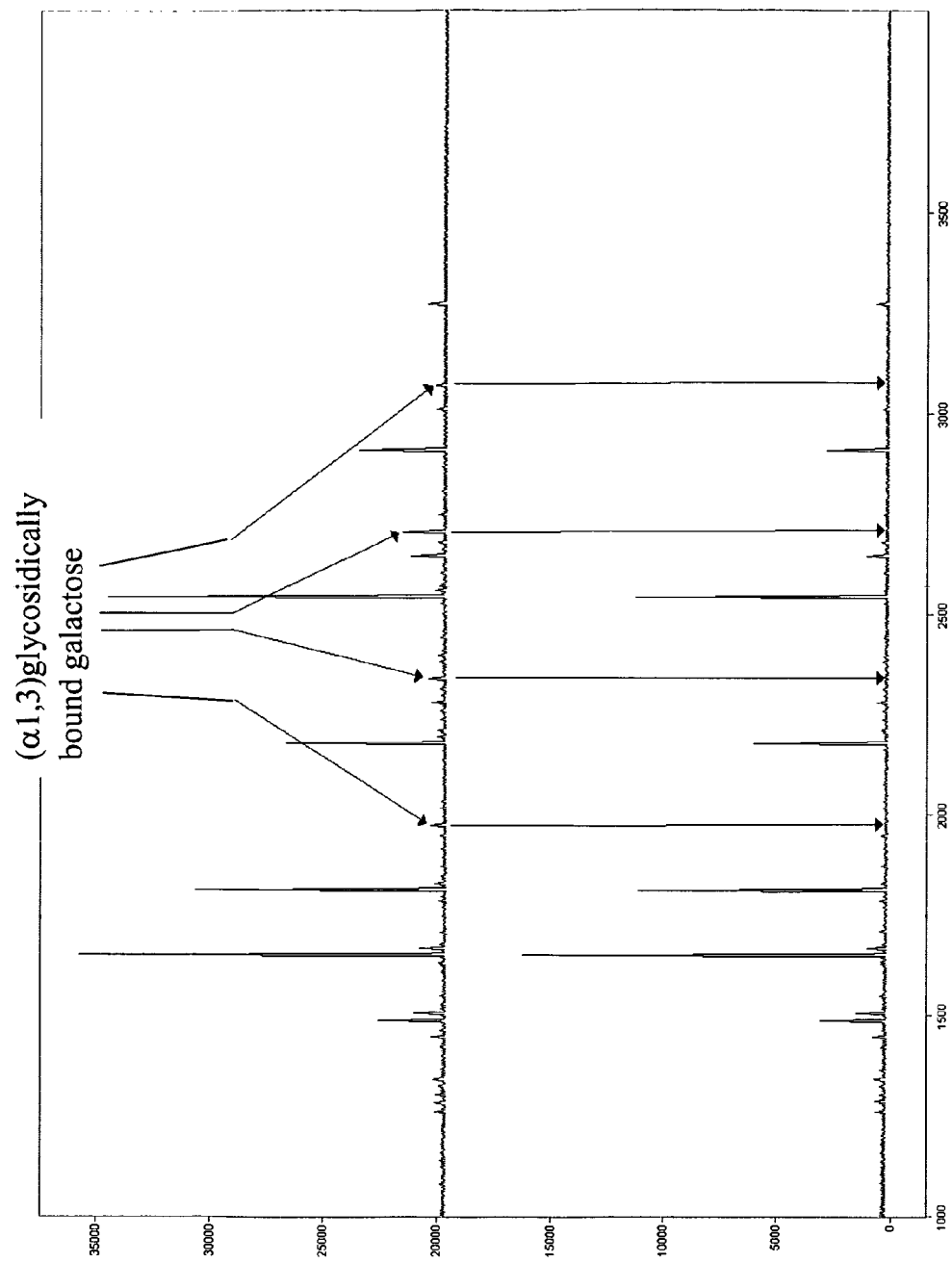
FIG. 3 Total ion chromatogram of the reference sample of a mutated IL15FC-Fc fusion polypeptide (upper part) and of the incubation with the ($\alpha$1,3)galactosidase from green coffee beans (lower part). It can be seen that ($\alpha$1,3)glycosidically bound galactose was removed completely and that this enzyme has no ($\beta$1,4)galactosidase activity.

The interleukin-15/Fc fusion protein has been prepared in accordance with the data and methods reported in the international patent applications WO 1997/041232, WO 2005/100394 and WO 2005/100395.

Example 2

Cleavage of ($\alpha$1,3)glycosidically Bound Galactose Residues

Digestion with $\alpha$-Galactosidase

The samples were adjusted to the corresponding buffer conditions by dialysis (see Table 2) and thereafter incubated with the enzyme.

For example:

40 ml of the interleukin-15/Fc fusion protein solution with a concentration of about 1 mg/ml were digested with 1.5 mL of ($\alpha$1,3)galactosidase (204 U/ml) over night (16 hours) at 25° C.

TABLE 2

| (α1,3)galactosidase from (EC 3.2.1.22) | buffer conditions | amount of interleukin-15/Fc fusion protein | amount of (α1,3)galactosidase | conversion conditions |
|---|---|---|---|---|
| Enzymatic digestion conditions | | | | |
| green coffee beans | 100 mM sodium citrate/phosphate (pH 6.0)* | 100 µg protein solution | 1 U | 37° C., 18 hours |
| Xanthomonas manihotis | 50 mM sodium acetate 5 mM CaCl$_2$ pH 5.5 | 100 µg protein solution | 840 U | 37° C., 18 hours |
| Escherichia coli | 250 mM sodium phosphate, pH 6.5* | 100 µg protein solution | 1 U | 37° C., 18 hours |

*according to the manufacturers' manual

Small Scale Purification with Protein A

The protein A column was equilibrated with 25 mM Tris (hydroxymethyl)aminomethane buffer (TRIS) containing 25 mM sodium chloride and 5 mM EDTA at pH 7.2. The samples were applied to the column, the column was washed with equilibration buffer end the fusion protein was eluted with 100 mM Citrate Buffer pH 3.6.

Sample Preparation for Mass Spectrometry

Samples containing 100 µg of the interleukin-15/Fc fusion protein were buffer exchanged by means of centricons to 2 mM TRIS-HCl, pH 7.0. 50 µl of the interleukin-15/Fc fusion protein were digested with 1 µl of N-glycosidase F and 1 µl sialidase to cleave the glycans from the protein and to eliminate sialic acid moieties.

Ion exchange resin AG 50W-X8 was suspended in water and was shaken several times. After settlement of the resin the water was discarded. This was done three times. 900 µl of the suspension were transferred to a MICRO Bio-Spin Chromatography Column and centrifuged for 1 minute.

The digested samples were applied to the column and the columns were centrifuged for 1 min. The purified glycans were collected in the flow-through. The obtained solutions were diluted 1:1 with sDHB matrix solution (sDHB in 125 µl ethanol and 125 µl 10 mM sodium chloride in water).

Alternatively, an aliquot of 1 µl digest were mixed with 1 µl of DHB matrix solution (10 mg DHB in 10 mM sodium chloride in water) and quickly dried using high vacuum to get homogenous spots for MALDI-TOF analysis.

Mass Spectrometry

Calibration spectra were acquired with a MALDI-TOF Mass Spectrometer Voyager DE Pro from Applied Biosystems in the Reflectron Mode. The Acceleration Voltage was set to 20000 V; Grid Voltage was 76% and the Mirror Voltage Ratio 1.12. The Extraction Delay Time was set to 110 ns. The Acquisition mass range was from 1000 to 5000 Da, the Laser Intensity was 2460 and the Laser Rep Rate 20.0 Hz.

The invention claimed is:

1. A method for producing an immunoglobulin or polypeptide comprising at least the CH2 domain and the CH3 domain of a full length immunoglobulin heavy chain with defined glycostructure comprising the following steps:
    providing an affinity chromatography column eluate containing the immunoglobulin or polypeptide; and
    incubating the affinity chromatography column eluate with an α-galactosidase of plant origin, which cleaves off the (α1,3) glycosidically bound galactose residue at the non-reducing end of the glycostructure in the CH2 domain of the immunoglobulin or polypeptide.

2. The method of claim 1, further comprising a third step wherein the incubated affinity chromatography eluate is applied to a protein A chromatography material and recovering the immunoglobulin or immunoglobulin fragment from the protein A chromatography material and thereby producing an immunoglobulin or immunoglobulin fragment with defined glycostructure.

3. The method according to claim 1, characterized in that the enzyme, which cleaves off the monosaccharide residue at the non-reducing end of the glycostructure in the CH2 domain of the immunoglobulin or immunoglobulin fragment, is (α1,3) galactosidase (EC 3.2.1.22) from green coffee beans.

4. The method according to claim 2, characterized in that the incubating the affinity chromatography column eluate with an enzyme, which cleaves off the monosaccharide residue at the non-reducing end of the glycostructure in the CH2 domain of the immunoglobulin or immunoglobulin fragment, comprises the following steps:
    incubating the affinity chromatography column eluate with an (α1,3)glycosidase;
    taking a sample from the incubation mixture;
    either
        applying the sample to protein A coated sepharose beads and afterwards washing the beads;
        recovering the immunoglobulin or immunoglobulin fragment from the protein A sepharose beads;
        adjusting the buffer conditions for glycosidase/sialidase digest; and
        incubating the immunoglobulin or immunoglobulin fragments with a glycosidase/sialidase to cleave of all N-Glycans,
    or
        applying the sample to protein A coated magnetic beads and afterwards washing the beads;
        incubating the beads with a glycosidase and recovering the cleaved off oligosaccharides; and
        purifying the cleaved off oligosaccharides with a cation exchange chromatography,
    determining the kind and amount of the monosaccharide residue at the non-reducing end of the glycostructure in the cleaved off oligosaccharides by mass spectrometry; and
    continuing the incubating until all monosaccharide residue at the non-reducing end of the glycostructure, which can be cleaved off by the enzyme, have been cleaved off.

5. The method according to claim 1, further comprising the following steps as first steps:
    providing a cell comprising a nucleic acid encoding the immunoglobulin or immunoglobulin fragment;
    cultivating the cell;
    recovering the immunoglobulin or immunoglobulin fragment from the cell or the cultivation medium, and
    applying the immunoglobulin or immunoglobulin fragment to a protein A chromatography material and recovering the immunoglobulin from the protein A chromatography material.

6. The method according to claim 4, further comprising the following step as a final step:
    purifying the produced immunoglobulin or immunoglobulin fragment with a defined glycostructure with one to three chromatography steps.

7. The method according to claim 5, characterized in that the cell is a mammalian cell.

8. The method according to claim 7, characterized in that the mammalian cell is a hamster cell, murine cell, a rabbit cell, a sheep cell, or a hybridoma cell thereof.

9. The method according to claim 7, characterized in that the cell is a CHO cell, a NS0 cell, a BHK cell or a SP2/0 cell.

10. The method according to claim 1, characterized in that the immunoglobulin or immunoglobulin fragment comprises amino acid residues 18 to 364 of SEQ ID NO:02.

* * * * *

SEQUENCE LISTING

```
<160> NUMBER OF SEQ ID NOS: 2

<210> SEQ ID NO 1
<211> LENGTH: 1113
<212> TYPE: DNA
<213> ORGANISM: Artificial Sequence
<220> FEATURE:
<223> OTHER INFORMATION: nucleic acid sequence of the human mutated
      IL15/Fc with CD5 leader peptide

<400> SEQUENCE: 1
atgcccatgg ggtctctgca accgctggcc accttgtacc tgctggggat gctggtcgct      60
tcctgcctcg gaaactgggt gaatgtaata agtgatttga aaaaaattga agatcttatt     120
caatctatgc atattgatgc tactttatat acggaaagtg atgttcaccc cagttgcaaa     180
gtaacagcaa tgaagtgctt tctcttggag ttacaagtta tttcacttga gtccggagat     240
gcaagtattc atgatacagt agaaaatctg atcatcctag caaacaacag tttgtcttct     300
aatgggaatg taacagaatc tggatgcaaa gaatgtgagg aactggagga aaaaaatatt     360
aaagaatttt tggacagttt tgtacatatt gtcgacatgt tcatcaacac ttcggatccc     420
aaatctgcta acaaaactca cacatgccca ccgtgcccag cacctgaact cctgggggga     480
ccgtcagtct tcctcttccc cccaaaaccc aaggacaccc tcatgatctc ccggaccccct    540
```

```
gaggtcacgt gcgtggtggt ggacgtgagc cacgaagacc ctgaggtcaa gttcaactgg    600
tacgtggacg gcgtggaggt gcataatgcc aagacaaagc cgcgggagga gcagtacaac    660
agcacgtacc gtgtggtcag cgtcctcacc gtcctgcacc aggactggct gaatggcaag    720
gagtacaagt gcaaggtctc caacaaagcc ctcccagccc ccatcgagaa aaccatctcc    780
aaagccaaag gcagccccg agaaccacag gtgtacaccc tgcccccatc ccgggatgag     840
ctgaccaaga accaggtcag cctgacctgc ctggtcaaag gcttctatcc cagcgacatc    900
gccgtggagt gggagagcaa tgggcagccg gagaacaact acaagaccac gcctcccgtg    960
ctggactccg acggctcctt cttcctctac agcaagctca ccgtggacaa gagcaggtgg   1020
cagcagggga acgtcttctc atgctccgtg atgcatgagg ctctgcacaa ccactacacg   1080
cagaagagcc tctccctgtc tccgggtaaa tga                                1113
```

```
<210> SEQ ID NO 2
<211> LENGTH: 370
<212> TYPE: PRT
<213> ORGANISM: Artificial Sequence
<220> FEATURE:
<223> OTHER INFORMATION: amino acid sequence of the human mutated
      IL15/Fc with CD5 leader peptide

<400> SEQUENCE: 2
```

Met Pro Met Gly Ser Leu Gln Pro Leu Ala Thr Leu Tyr Leu Leu Gly
1               5                   10                  15

Met Leu Val Ala Ser Cys Leu Gly Asn Trp Val Asn Val Ile Ser Asp
            20                  25                  30

Leu Lys Lys Ile Glu Asp Leu Ile Gln Ser Met His Ile Asp Ala Thr
        35                  40                  45

Leu Tyr Thr Glu Ser Asp Val His Pro Ser Cys Lys Val Thr Ala Met
    50                  55                  60

Lys Cys Phe Leu Leu Glu Leu Gln Val Ile Ser Leu Glu Ser Gly Asp
65                  70                  75                  80

Ala Ser Ile His Asp Thr Val Glu Asn Leu Ile Ile Leu Ala Asn Asn
                85                  90                  95

Ser Leu Ser Ser Asn Gly Asn Val Thr Glu Ser Gly Cys Lys Glu Cys
            100                 105                 110

Glu Glu Leu Glu Glu Lys Asn Ile Lys Glu Phe Leu Asp Ser Phe Val
        115                 120                 125

His Ile Val Asp Met Phe Ile Asn Thr Ser Asp Pro Lys Ser Ala Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr

-continued

```
                260                 265                 270
Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
370
```